United States Patent
Vallana et al.

(10) Patent No.: US 6,491,720 B1
(45) Date of Patent: Dec. 10, 2002

(54) ANGIOPLASTY STENT ADAPTED TO COUNTER RESTENOSIS RESPECTIVE KIT AND COMPONENTS

(75) Inventors: Franco Vallana, Turin (IT); Maria Curcio, Saluggia (IT); Giovanni Rolando, Chivasso (IT)

(73) Assignee: Sorin Biomedica S.p.A., Saluggia (IT)

( * ) Notice: Subject to any disclaimer, the term of this patent is extended or adjusted under 35 U.S.C. 154(b) by 91 days.

(21) Appl. No.: 09/632,042

(22) Filed: Aug. 3, 2000

(30) Foreign Application Priority Data

Aug. 5, 1999 (IT) .......................... TO99A0693

(51) Int. Cl.[7] .................................. A61F 2/06
(52) U.S. Cl. ................. 623/1.42; 623/1.44; 623/1.15; 606/191; 606/192; 606/194
(58) Field of Search ................ 623/23.7, 1.1, 623/1.13–1.15, 1.32, 1.33, 1.42–1.54; 606/191–195, 198; 600/36

(56) References Cited

U.S. PATENT DOCUMENTS

| | | |
|---|---|---|
| 4,952,312 A | 8/1990 | Zantonelli et al. |
| 5,342,348 A | 8/1994 | Kaplan |
| 5,383,928 A | 1/1995 | Scott et al. |
| 5,637,113 A | 6/1997 | Tartaglia et al. |
| 5,674,242 A | 10/1997 | Phan et al. |
| 5,693,085 A * | 12/1997 | Buirge et al. ............... 606/192 |
| 5,700,286 A | 12/1997 | Tartaglia et al. |
| 5,707,385 A | 1/1998 | Williams |
| 5,725,567 A | 3/1998 | Wolff et al. |
| 5,733,327 A | 3/1998 | Igaki et al. |
| 5,769,883 A | 6/1998 | Buscemi et al. |
| 5,776,184 A | 7/1998 | Tuch |
| 5,885,609 A | 3/1999 | Amiji |
| 6,013,099 A | 1/2000 | Dinh et al. |
| 6,053,900 A * | 4/2000 | Brown et al. ............... 604/500 |
| 6,129,757 A | 10/2000 | Weadock |
| 6,156,373 A * | 12/2000 | Zhong et al. ............... 427/2.28 |
| 6,206,915 B1 | 3/2001 | Fagan et al. |

FOREIGN PATENT DOCUMENTS

| | | |
|---|---|---|
| EP | 0 441 516 A2 | 8/1991 |
| EP | 0 806 190 A1 | 11/1997 |
| EP | 0 847 766 A2 | 6/1998 |
| EP | 0 850 604 A2 | 7/1998 |
| EP | 0 857 470 A2 | 8/1998 |
| EP | 0 873 732 A1 | 10/1998 |
| EP | 0 875 215 A1 | 11/1998 |
| EP | 0 895 759 A1 | 2/1999 |
| EP | 0 895 760 A1 | 2/1999 |
| EP | 0 941 740 A2 | 9/1999 |
| WO | WO 95/03356 | 2/1995 |
| WO | WO 99/32167 | 7/1999 |
| WO | WO 00/12147 | 9/2000 |

OTHER PUBLICATIONS

*Textbook of Interventional Cardiology*, ed. Eric J. Topol, W.B. Saunders Company, 1994, and in particular Section IV of vol. II entitled "Coronary Stenting".

European Search Report for EP 00 83 0413 (3 pages).

\* cited by examiner

*Primary Examiner*—Corrine McDermott
*Assistant Examiner*—Urmi Chattopadhyay
(74) *Attorney, Agent, or Firm*—Popovich & Wiles, P.A.

(57) ABSTRACT

A stent structure includes a stent and one or more fibers disposed on the stent, the fiber adapted to provide a therapeutic agent. Nuclei containing therapeutic agents that impede restenosis may be included within the fiber or within separate particles that are contained within hollow core fibers. The fibers and the particles may be bioerodible. A permeable, biocompatible sheath may be interposed between the stent and the fiber. A kit including a stent, a fiber, and a delivery catheter is also described.

26 Claims, 4 Drawing Sheets

ANGIOPLASTY STENT ADAPTED TO COUNTER RESTENOSIS RESPECTIVE KIT AND COMPONENTS

This application claims benefit to foreign application IT TO99A000693 filed in Italy on Aug. 5, 1999.

FIELD OF THE INVENTION

The present invention relates to angioplasty stents. In particular, this invention relates to a stent structure that minimizes restenosis.

BACKGROUND OF THE INVENTION

The term "stent" is used to indicate in a general way those devices intended for intravascular application (for example inside a blood vessel), usually carried out by catheterization followed by in-situ expansion in order to exert an action of local support to the lumen.

For a general overview of vascular stents the reader may usefully refer to the work "Textbook of Interventional Cardiology", ed. Eric J. Topol, W.B. Saunders Company, 1994, and in particular section IV of vol. II entitled "Coronary Stenting".

The subject has also attracted a large number of patent documents, as witness, for example, EP-A-0 806 190, EP-A-0 850 604, EP-A-0 847 766, EP-A-0 857 470, EP-A-0 875 215, EP-A-0 895 759, EP-A-0 895 760.

The clinical use of these devices, which in recent years has grown considerably in popularity, must address the need to ensure an effective impediment to the phenomenon usually known as restenosis. This is a phenomenon (linked to the manifestation of physiological mechanisms that, furthermore, are not yet clearly understood) whereby the stenosis site, after having been reopened by the implant of the stent, gradually tends to close up again, usually owing to gradual tissue growth.

Various solutions have been proposed for dealing with this problem: they essentially involve a local action designed to impede the phenomena that give rise to the restenosis. In particular, a number of solutions have been investigated in which drugs are released locally or radioactive sources are used locally.

These solutions, especially those based on the localized and controlled release of drugs, have themselves to address the problem of how this localization is to be effectively carried out at the stent implant site. In the case of agents designed to be released by the stent, it is important to ensure that the majority of the agents are released gradually into the walls of the vessel rather than being washed away relatively rapidly by the flow of blood passing through the lumen of the stent. This is particularly important because clinical experiments show that the mechanisms of reaction of the vessel subjected to the stent implant occur at the level of a reaction by the vessel wall within a period of time typically ranging from 1 to 6 months from implantation.

SUMMARY OF THE INVENTION

It is an object of the present invention to provide a solution capable of improving on previously attempted solutions, from a number of points of view. First, it is wished to be able to achieve a reliable connection, or anchoring, of therapeutic agents to the stent, and in particular a connection that will not be influenced either by the movement of the stent as it dilates, which is characteristic of the implanting operation, or by possible surface treatments (such as deposition of a surface layer of biocompatible carbon-containing material) which may have been applied to the stent.

Second, it is wished to be able to produce a collection of components capable of acting in effect as a "releasing machine" that will deliver a controlled release of restenosis-impeding agents, particularly as regards the possibility of precisely controlling the release kinetics, with the further possibility of selectively controlling, in time or in relation to other parameters, the release of diverse agents.

Again, it is wished that the functions specified above be able to be carried out without negative impacts on the other characteristic aspects of the functionality of the stent, e.g., by ensuring that, whether at the time of implantation or later, the lumen of the stent does not become a site for obstructions to the free flow of blood.

In one aspect, this invention is stent structure having a longitudinal axis and having a substantially tubular body capable of being dilated from a radially-contracted position to a radially-expanded position comprising a stent having an inner surface and an outer surface; and at least one fiber disposed adjacent one of the surfaces of the stent, the fiber adapted to provide a therapeutic agent. Preferably, the therapeutic agent is an agent that impedes restenosis. The fibers preferably are attached to the stent structure such that the fibers do not substantially retard dilation of the stent structure from the radially contracted position to the radially expanded position. The therapeutic agent may be contained within a nucleus embedded in the at least one fiber or may be within a lumen defined by the at least one fiber. The therapeutic agent may be in a nucleus where the nucleus is in a particle contained within an outer envelope. Preferably, the outer envelope is bioerodible. The particle may range in size from 100 to 200 nanometers. Preferably, the fiber is bioerodible.

The stent structure may also comprise a sheath interposed between the stent and the fiber. The sheath may be a biocompatible material, such as silicone, and may be permeable. Alternatively, the sheath may comprise a metallic material or a polymeric material and have an apertured structure such as a mesh, so that it may expand when the stent structure expands. The sheath may be coated with a layer of a biocompatible carbon-containing material. The fiber may be anchored to the sheath. There may be multiple fibers disposed around the stent. The fiber preferably is extensible in the direction of the longitudinal axis. The fiber may be wound around the stent structure in a helical path with a winding pitch of 45° or 60° relative to the longitudinal axis. The fiber may comprise a porous structure. The fiber diameter can range between about 30 and 100 micrometers and have wall thickness ranging between about 10 and 20 micrometers. The therapeutic agent may comprise one or more drugs selected from anti-inflammatory and antimitotic agents.

In a second embodiment, this invention is a kit for impeding restenosis in vasculature comprising a stent that can be dilated from a radially contracted position to a radially expanded position; at least one fiber comprising a restenosis-impeding agent; a catheter adapted to deliver the stent and the at least one fiber to a site of restenosis; and a container configured to house the stent, the at least one fiber, and the catheter. The fiber may comprise a sheet configured to be wound around the stent or a tubular sock configured to be fitted onto the stent.

In a third aspect, this invention is a component for delivering a therapeutic agent that impedes restenosis, the component for use in combination with a stent having a longitudinal axis and having an inner surface and an outer surface, the component comprising at least one fiber configured to be placed adjacent a surface of the stent; a particle contained by the at least one fiber, and a nucleus contained within the particle, the nucleus adapted to contain the therapeutic agent. The particle may be contained within a lumen defined by the at least one fiber and/or may comprise the nucleus contained within an outer envelope. The therapeutic agent that impedes restenosis may further comprise one or more drugs selected from anti-inflammatory and antimitotic agents.

In a fourth aspect, this invention is a method of impeding restenosis in a patient's vasculature comprising: providing a stent having an inner surface and an outer surface and a longitudinal axis and being capable of being dilated from a radially-contracted position to a radially-expanded position; providing at least one fiber adapted to deliver a restenosis impeding agent; providing a delivery catheter; mounting the stent and the at least one fiber onto the delivery catheter; and advancing the delivery catheter to the patient's vasculature to deliver the stent and the at least one fiber at the site of stenosis.

BRIEF DESCRIPTION OF THE DRAWINGS

The invention will now be described, purely by way of non-restrictive example, with reference to the accompanying drawings, in which.

DETAILED DESCRIPTION OF THE PREFERRED EMBODIMENTS

Figure 1:
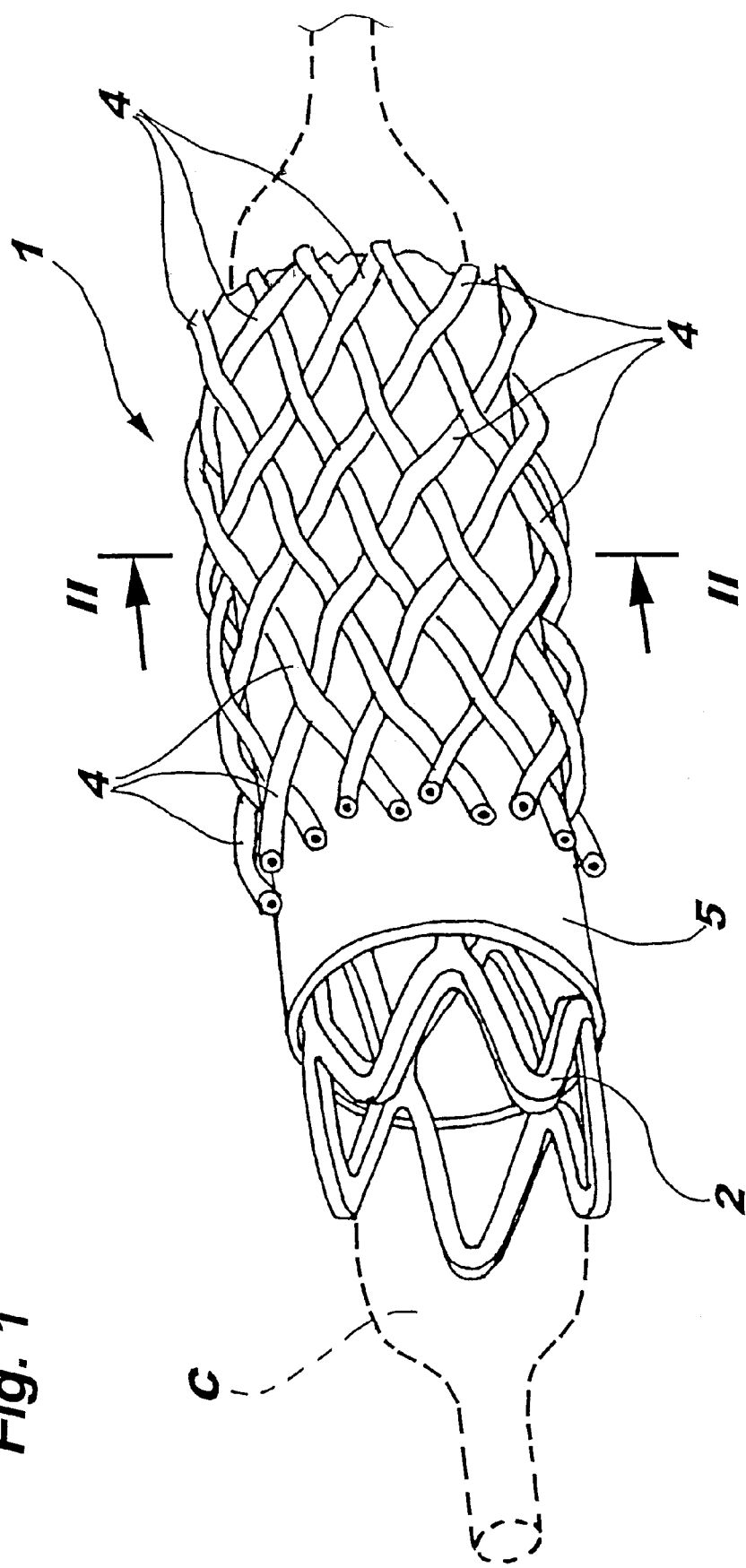
FIG. 1 is a perspective view, with some parts removed for clarity of illustration, of the preferred angioplasty stent structure of the invention.

In FIG. 1, reference number 1 indicates a preferred embodiment of the angioplasty stent structure of the invention. For a general identification of the modes of use and production features of such an implant device, refer to the documentation cited in the introductory part of this description.

By way of an overview, it will be recalled that stent structure 1 is usually produced as a generally tubular body, with a total length usually varying from a few millimeters to tens of millimeters and a wall thickness (the wall usually having an open structure of links or loops) of the order of, for example, a few hundredths of a millimeter (mm). These features are all with a view to the possible insertion of the stent into a lumen (such as a blood vessel), in a site suffering from stenosis which is to be corrected. The stent is moved into position, e.g., by catheterization, and than expanded radially from its diameter of insertion, which is of the order of about 1 mm, to an expanded diameter of the order of about 3 to 5 mm. In the expanded condition the stent supports the lumen and eliminates the stenosis. The outside diameter when radially contracted is selected so as to allow the stent to be inserted into the lumen where the treatment is being carried out, while the expanded diameter corresponds generally to the desired diameter that establishes and maintains the lumen once the stenosis has been eliminated.

Although the principal application of the stent described above refers to the treatment of blood vessels, it is possible (and therefore included within the scope of the invention) to fit it as a support for any lumen present in the human or animal body.

As far as the methods and principles that enable the stent to be opened (i.e., expanded in situ) are concerned, the solution that is most widely used at present is to employ what is known as a balloon catheter. The stent is mounted around the balloon of the catheter in its contracted condition and the balloon is expanded once the stent has been delivered to the site of the implant (see, for example, FIG. 1, where the outline of the catheter balloon, labeled C, has been indicated schematically in broken lines). However, other methods may also be envisaged, such as that of employing superelastic materials which expand the stent once the containment components, designed to keep the stent contracted until it reaches the site of the implant, have been removed. Additionally or alternatively it has also been suggested that the stent be made from materials having a so-called "shape memory" enabling it to be expanded radially in the implant position.

Usually, as is known in the art, the stent is made from a metallic material that reconciles two fundamental requirements for application, that is an ability to deform plastically during the expansion and an ability to maintain its expanded form by resisting stresses that would tend to re-close the stent.

These technological issues will not be discussed in detail in the present description inasmuch as they are not in themselves relevant to an understanding of the embodiment of the invention. This is essentially true also for the technology of manufacture of the stent (manufacture from a continuous tubular preform, manufacture from a striplike body which is then closed into a tube, manufacture from a shaped metal wire, etc.).

Figure 2:
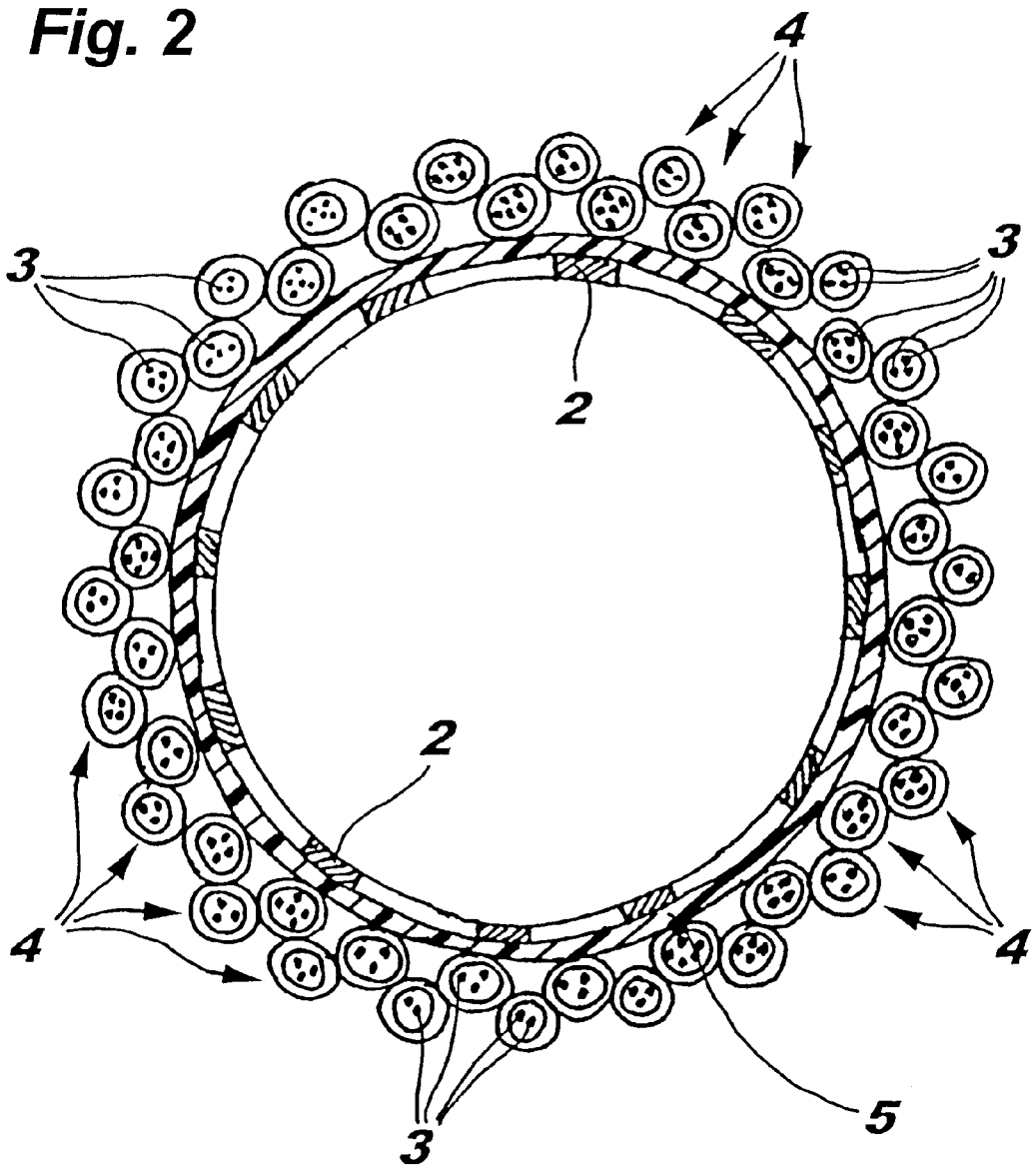
FIG. 2 is an enlarged cross-sectional view along line II—II of the stent structure of FIG. 1.

FIGS. 1 and 2 illustrate stent structure 1, comprising stent 2, sheath 5, and one or more fibers 4 disposed around sheath 5. Stent structure 1 is delivered to the vasculature by means of catheter C, as described above. Stent structure 1 is a generally tubular body capable of being selectively expanded radially by the principles described above. In other words the solution according to the present invention is in fact quite "transparent" or at any rate not appreciably influenced by the specific characteristics of geometry, treatment and technology of manufacture of stent 2.

Fiber 4 is adapted to deliver a therapeutic agent such as a restenosis impeding agent. Fiber 4 may have restenosis impeding agents embedded in it or inside of it. Fiber 4 may have hollow core 40 surrounded by wall 42. Core 40 can be filled with particles comprising a desirable restenosis preventing agent. Alternatively, therapeutic agents may be disposed within the fiber wall. Before turning to a more detailed explanation of the characteristics of stent structure 1, it is useful to refer to FIGS. 3 to 7, which show a number of the components used to make the stent structure of this invention.

Figure 5:
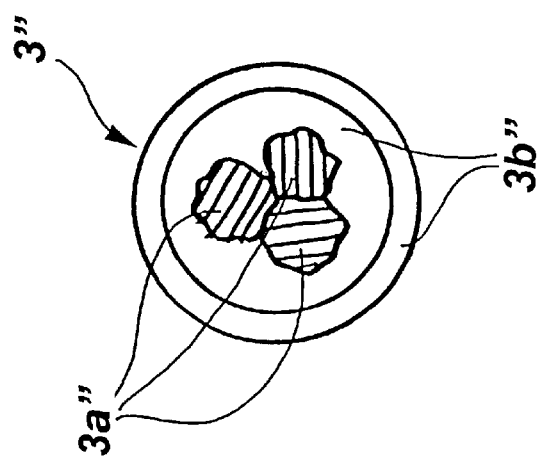
FIGS. 3 to 5 are cross-sectional views of the particles illustrated in FIG. 2.
Figure 4:
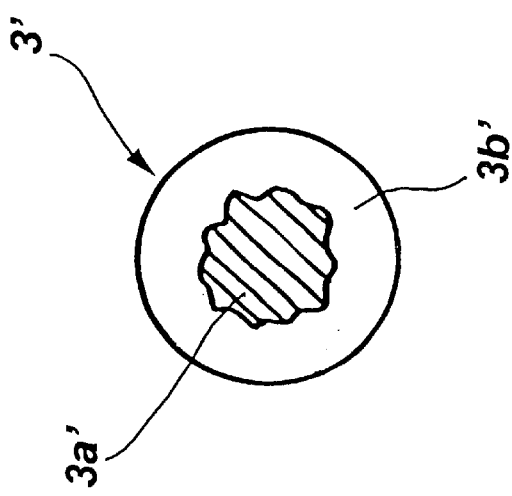
Figure 3:
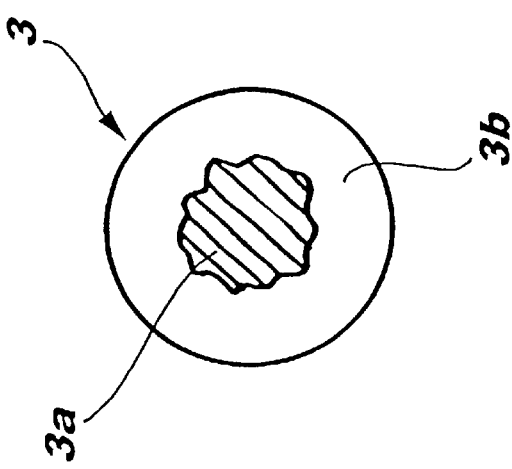

Specifically, FIGS. 3 to 5 illustrate, in a number of possible variants, particles 3, 3' and 3", respectively. Preferably these particles are spherical or substantially spherical in shape and have typical diameters of the order of hundreds of nanometers. Particles of this size ate referred to as "nanoparticles". FIG. 3 illustrates particles 3 comprising nucleus 3a surrounded by outer envelope 3b. FIG. 4 illustrates nucleus 3a' that is similar in size to nucleus 3a of FIG. 3, except that outer envelope 3b' is smaller than 3b, resulting in a smaller particle that can deliver the same amount of therapeutic agent. FIG. 5 shows that nucleus 3a" and/or envelope 3b" may have a complex structure (i.e., 3a" having two or more nuclei and/or 3b" having a stratified, or multi-layer, outer envelope). Further, particles having multiple nuclei may be able to deliver more than one therapeutic formulation. It is also possible for the nuclei 3a, 3a', or 3a" not to be in the approximate center but instead be eccentric relative to the envelope 3b, 3b', or 3b", respectively. The rest of this description will however refer for simplicity's sake to nucleus 3a and to envelope 3b of substantially uniform, homogeneous structure and substantially concentric with each other.

Nucleus 3a includes a therapeutic agent capable of exerting an antagonism towards restenosis by the effect of an action of localized release and/or selective penetration into the walls of the vessel where the stent is implanted. Nucleus 3a also may comprise, for example, a drug or collection of drugs whose action is anti-inflammatory, antimitotic and/or promotes the processes of repair of the vessel wall such as to mitigate or prevent the reactions on which the process of restenosis is based. However, the particular choice of agent and/or collections of agents is not specifically the subject-matter of the present invention.

The above remarks also apply to the manufacture of the envelope 3b. Outer envelope 3b of particle 3 comprises any substance that can be described as "bioerodible". This expression is intended here to denote any substance which, within the context of the present invention (namely implantation in a lumen), tends to be consumed and/or to adopt or demonstrate a porous morphology or any morphology such as to allow the outward diffusion of the substance or substances contained inside nucleus 3a. The properties of bioerodibility described are typically accompanied by properties of biocompatibility and biodegradability which are important in this specific application.

One choice for the production of envelope 3b is polyethylene glycol (PEG) or polylactic-glycolic acid (PLGA) as the constituent material. The method of production of these is known in the art.

The corresponding release kinetics can be controlled (especially as regards the time required to achieve outward diffusion of the agents contained inside the nucleus 3a) by varying, individually or in combination, the following parameters:

the composition of the nucleus 3a, the composition of the envelope 3b, the thickness of the envelope 3b, the relative location of the nucleus 3a with respect to the envelope 3b, the structure (homogeneous, multiple and/or stratified) of the nucleus 3a, and the structure (homogeneous, multiple, stratified and/or porous) of the envelope 3b.

FIGS. 3 and 4 illustrate, purely by way of example, the option of producing two particles 3 containing nuclei 3a with dimensions roughly equal to each other in combination with envelopes 3b of differing thicknesses. In all cases the principles, methods and technologies relating to the production of nanoparticles such as the nanoparticles 3 shown in FIGS. 3 to 5 should be taken to be well known in the art.

The above remarks also apply in substance to the option of having nanoparticles 3, 3', and 3", such as those shown in FIGS. 3 to 5, respectively, to (whether identical to each other or not) accompany fibers 4 that are also preferably made from bioerodible materials such as the materials cited earlier.

The production of fibers 4 and their provision with nanoparticles 3 correspond to known solutions. In particular, the production of microfibers in the form of hollow-fiber membranes is well known and well established at the technological level in the manufacture of devices such as dialyzers or oxygenators of the blood.

Figure 6:
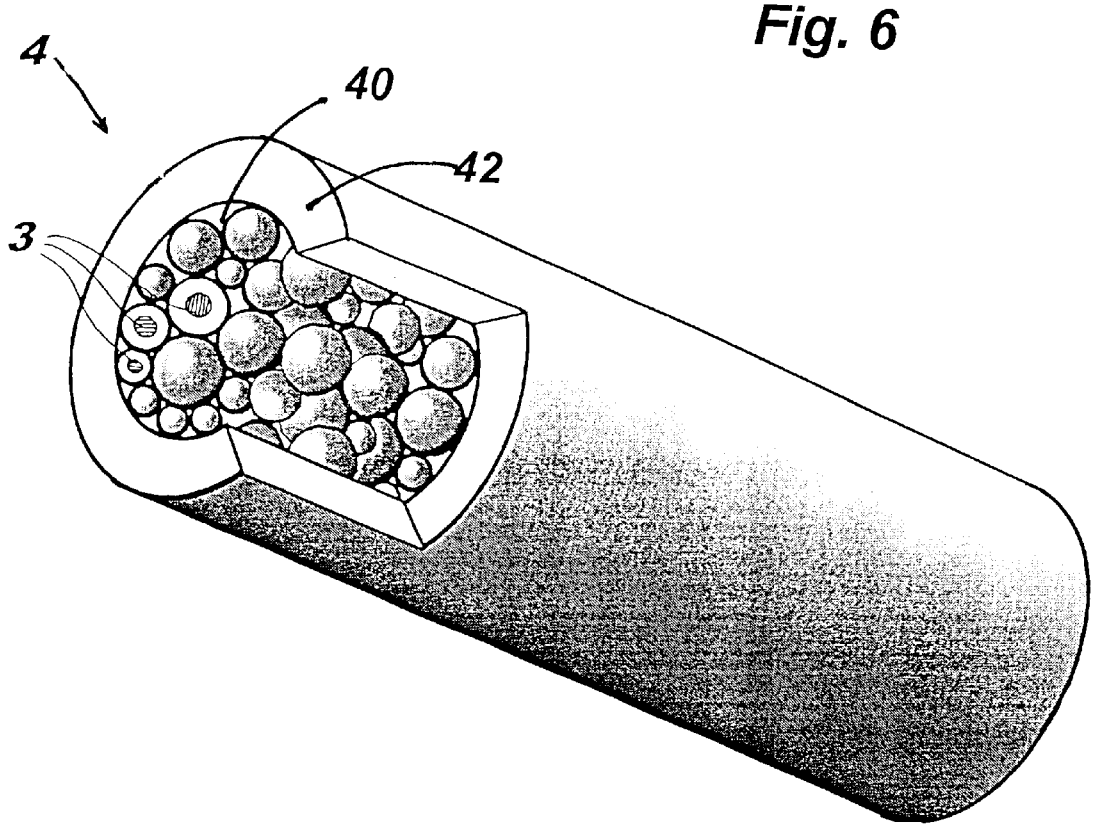
FIGS. 6 and 7 illustrate perspective views of fibers used in a preferred embodiment of the stent structure of FIG. 1.
Figure 7:
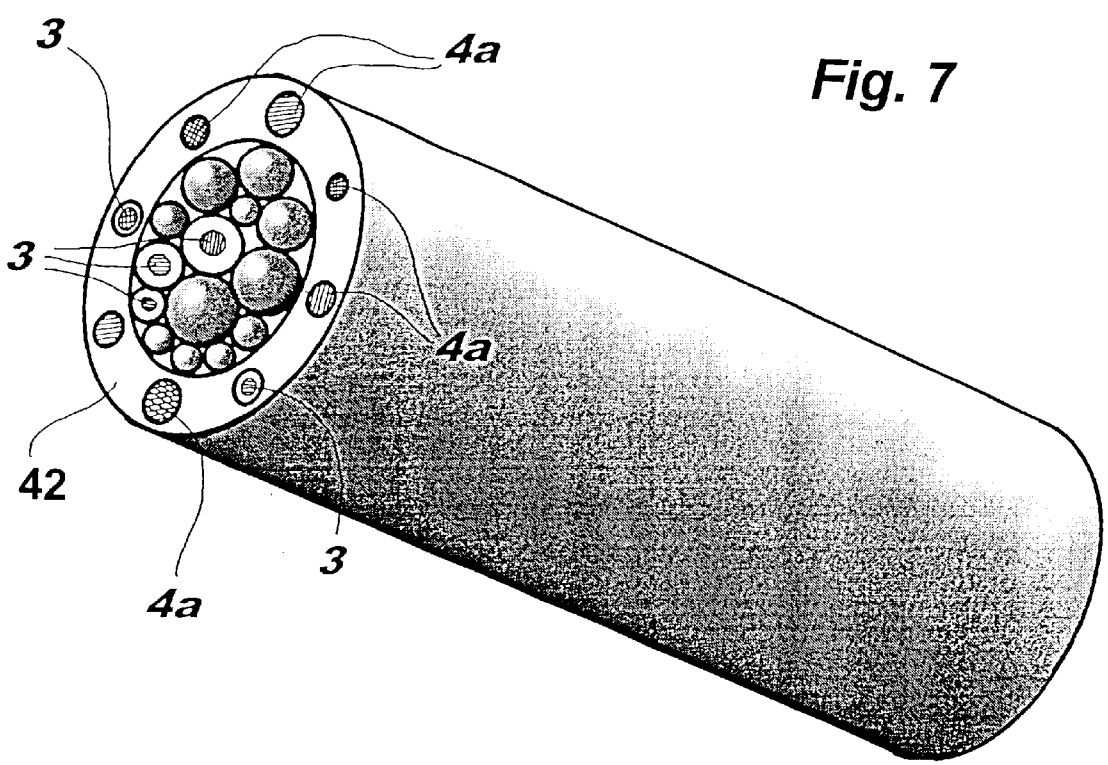

FIG. 6 illustrates fiber 4 having hollow core 40 and wall 42. Hollow core 40 is filled with nanoparticles 3. Alternatively, or additionally, as shown in FIG. 7, wall 42 of hollow core fiber 4 may contain nuclei 4a. The fiber thus acts as an erodible support. Nuclei 4a may be the same composition as described above for nuclei 3a and thus provide an additional means to convey restenosis-impeding agents when stent structure 1 is implanted. It is also contemplated to use, at least locally in the environment of stent structure 1, fibers 4 that do not allow for the placing of nanoparticles 3 in lumen or core 40 of fibers 4. In this case, the fact that fibers 4 have hollow-fiber characteristics is not critical, and the use of fibers 4 of compact structure, having no hollow core, is therefore also possible. By analogy, with reference to the diagram of FIG. 6, it is possible to use porous hollow core fibers 4 of a non-bioerodible material that would act exclusively as containers for nanoparticles 3. Porous fibers would allow the diffusion of the agents carried by nuclei 3a of nanoparticles 3.

To give some idea of dimensions, fiber 4 (as shown in the drawings) may have diameters ranging between about 30 and 100 micrometers, with wall thicknesses typically ranging between about 10 and 20 micrometers, and therefore with corresponding dimensions of its lumen or axial cavity ranging between about 10 and 60 micrometers. A sufficient length of fiber is chosen such that a desired amount of the restenosis-impeding agent is delivered.

FIGS. 1 and 2 illustrate that fibers 4 may attach to stent 2 of stent structure 1 in one or more layers. The fibers optionally may be interlinked with stent 2 by using the open configuration of stent 2. In a preferred embodiment, fibers 4 are wound around stent 2. The winding arrangement (or more generally the placement) of fibers 4 on stent 2 must of course take account of the fact that fibers 4 are normally laid on stent structure 1 when the latter is in its radially contracted position and must not therefore be damaged or altered in their functionality by the radial expansion which typifies the operation of implanting the stent structure. That is, fibers 4 are attached to stent 2 in such a way as to present virtually no resistance to the dilation characteristic of the stent.

This result can be achieved in several different ways. In the example of an embodiment illustrated here, fibers 4 have been wound around the structure of the stent by known processes and devices (as described in, for example, U.S. Pat. No. 4,952,312 (Zantonelli et al.)) hereby incorporated herein by reference, in such a way that the angle formed by the fibers relative to the family of planes perpendicular to the longitudinal axis of the stent (in practice the angle of winding of the helical path defined by each fiber) is relatively great, preferably at least 45° and still more preferably greater than 60°. Alternative solutions are of course possible, such as for example that of making fibers 4 from elastic materials and/or that of causing fibers 4 to follow a sinuous path; the purpose being to ensure the fibers can stretch in the longitudinal direction.

For the purpose of laying fibers 4 on stent 2 it is also possible to exploit the presence (initially dictated by other reasons explained below) of sheath or tunic 5 interposed between structure 2 and the layer or layers of fibers 4 laid around it. Specifically, it is possible to consider applying fibers 4 to stent 2 of stent structure 1 by connecting them (e.g., by an adhesive connection) to the outer surface of sheath 5. In this embodiment it is possible to locate fibers 4 (whether ordered in a single layer or whether present in two or more layers) so that fibers 4 run generally along the generatrices of the imaginary cylindrical surface defined by stent structure 1. A solution of this kind would ensure that the movement of radial dilation of stent 2 has no effect on fibers 4.

The main purpose of sheath 5 is to prevent the undesirable prolapse of fibers 4 into the lumen of the stent structure 1. Prolapse can occur, for example, if stent 2—whether in its entirety or even only partly—has a highly apertured configuration. Accordingly, sheath 5 has the function of ensuring that, even following implantation, fibers 4 preferably stay outside stent 2 and are interposed between the stent structure 1 and the vessel wall.

The presence of sheath 5 is also beneficial at later stages, namely when the agents present in nuclei 3a and 4a are diffused. This is because sheath 5 is able to act at least partly as a barrier and so ensure that the release of the above-mentioned active agents takes place preferably and primarily towards the wall of the vessel and not towards the interior lumen of stent 2, which would mean that blood flowing through the lumen would wash the active agents away.

For the manufacture of sheath 5, it is possible to employ various materials, preferably with good biocompatibility properties, whether owing to the nature of the constituent material or to the fact that sheath 5 has been subjected to a treatment such as surface deposition of a layer of biocompatible carbon-containing material. An option that is thought preferable is to make sheath 5 from a silicone material. Alternative options are of course possible, such as making sheath 5 in the form of a tunic of a metallic or polymeric net having an apertured structure, such as a fine mesh capable of reproducing the movement of the stent as it expands.

The option of making sheath 5 with general characteristics of porosity (or more generally of permeability, which may be more effective on substances moving out through the stent structure than on substances moving in the opposite direction) is advantageous because it promotes contact between the vessel wall and the blood flowing through the stent, while at the same time preventing the flushing away of the active agents.

Fibers 4 can be laid on the structure 2 at different stages of the process of manufacture and/or preparation for the use of the stent 1. In particular (irrespective of the principles whereby fibers 4 are applied to stent 2) fibers 4 can be applied in the final stages of manufacture of the stent structure and thus before the stent structure is mounted on catheter C used for its delivery to the site. Alternatively, the fibers can be applied after stent 2 (and, optionally, sheath 5) has been mounted on the implanting catheter.

The collection of fibers 4 can therefore constitute a component of a kit which, in a form currently preferred for marketing, constitutes the product made available for the purposes of the implanting operation. The kit comprises a stent, the fiber(s), and a delivery or implanting catheter in a container adapted to hold the various components. Suitable containers include flexible pouches and rigid containers, such as plastic containers.

As another alternative it is possible to attach the fibers to the stent structure at an even later stage, that is immediately before proceeding to implant the stent (before or after the stent has been positioned on the implanting catheter). For this reason the fibers 4 may constitute an independent product or component capable of being marketed, e.g., in different versions included in an assortment and characterized by the presence of different kinds of agent and/or different kinetics of release. In particular this product may take the form of, for example, a small sheet (e.g., a piece of fabric that may be woven, non-woven, knitted, or the like) designed to be wound around the stent or may take the form of a tubular sock for fitting onto the stent.

It is clear from the above that this invention provides a "releasing machine" for the controlled release of restenosis-impeding agents. In particular, the dimensions of nanoparticles 3 and of nuclei 3a or 4a are such that even within the limits of a structure of small dimensions such as a stent it is possible to have a very large number of nuclei. Consequently the natures and properties of the impeding agents are available over a wide range of choices. As to the release kinetics, it is important to note that this invention makes it possible to act both at the level of nanoparticles 3 and at the level of fibers 4, for example by altering the composition, thickness or structure (making it homogeneous, stratified and/or porous) of the fibers 4, as well as on the location of the nuclei within the fibers (locating them directly, as in the case of the nuclei 4a, or indirectly by incorporating them in nanoparticles 3 which in turn are incorporated in the wall of a fiber). There is also the option of modifying the further parameter represented by the optional porosity of sheath 5.

Of particular interest is the possibility of operating in a combined way on the above-mentioned parameters, by, for example, causing the agents contained in nuclei 3a or 4a to diffuse over different time periods to those of the agents contained in other nuclei 3a or 4a in order that the restenosis-impeding action exactly keeps pace with the manifestation of the phenomena that give rise to restenosis itself. As an example, it may be decided that the release of anti-inflammatory drugs and/or promoters of vessel-wall repair processes should predominate in the acute phases, while antimitotic agents should be released predominantly at a later stage.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

What is claimed is:

1. A stent structure having a longitudinal axis and having a substantially tubular body capable of being dilated from a radially-contracted position to a radially-expanded position comprising:

a stent having an inner surface and an outer surface;

a sheath disposed on the outer surface of the stent; and at least one fiber disposed over the sheath, the at least one fiber adapted to provide a therapeutic agent.

2. The stent structure of claim 1 wherein the fibers do not substantially retard dilation of the stent structure from the radially contracted position to the radially expanded position.

3. The stent structure of claim 1 wherein the therapeutic agent is contained within a nucleus embedded in the at least one fiber.

4. The stent structure of claim 1 wherein the therapeutic agent is contained within a lumen defined by the at least one fiber.

5. The stent structure of claim 4 wherein the therapeutic agent is contained within a nucleus in a particle, the particle comprising the nucleus contained within an outer envelope.

6. The stent structure of claim 5 wherein the outer envelope is bioerodible.

7. The stent structure of claim 5 wherein the particle ranges in size from 100 to 200 nanometers.

8. The stent structure of claim 4 wherein the at least one fiber has a wall thickness ranging between about 10 and 20 micrometers.

9. The stent structure of claim 1 wherein the at least one fiber is bioerodible.

10. The stent structure of claim 1 further comprising a sheath comprises a biocompatible material.

11. The stent structure of claim 1 wherein the sheath comprises silicone.

12. The stent structure of claim 1 wherein the sheath is permeable.

13. The stent structure of claim 1 wherein the sheath comprises one of a metallic material or a polymeric material.

14. The stent structure of claim 13 wherein the sheath has an apertured structure.

15. The stent structure of claim 1 wherein the sheath is coated with a layer of a biocompatible carbon-containing material.

16. The stent structure of claim 1 wherein the at least one fiber is anchored to the sheath.

17. The stent structure of claim 1 wherein the at least one fiber is multiple fibers.

18. The stent structure of claim 1 wherein the at least one fiber is extensible in the direction of the longitudinal axis.

19. The stent structure of claim 1 wherein the at least one fiber is comprises a porous structure.

20. The stent structure of claim 1 wherein the at least one fiber has a diameter ranging between about 30 and 100 micrometers.

21. The stent structure of claim 1 wherein the therapeutic agent comprises an agent that impedes restenosis.

22. The stent structure of claim 1 wherein the therapeutic agent comprises one or more drugs selected from anti-inflammatory and antimitotic agents.

23. A stent structure having a longitudinal axis and having a substantially tubular body capable of being dilated from a radially-contracted position to a radially-expanded position comprising:
   a stent having an inner surface and an outer surface; and
   at least one fiber disposed adjacent one of the surfaces of the stent, the at least one fiber adapted to provide a therapeutic agent, the therapeutic agent being contained within a nucleus embedded in the at least one fiber.

24. A stent structure having a longitudinal axis and having a substantially tubular body capable of being dilated from a radially-contracted position to a radially-expanded position comprising:
   a stent having an inner surface and an outer surface; and
   at least one fiber disposed adjacent one of the surfaces of the stent, the at least one fiber adapted to provide a therapeutic agent, wherein the therapeutic agent is contained within a nucleus in a particle and the particle comprising the nucleus is contained within an outer envelope.

25. The stent structure of claim 24 wherein the outer envelope is bioerodible.

26. The stent structure of claim 24 wherein the particle ranges in size from 100 to 200 nanometers.

* * * * *